(12) United States Patent
Weiss (10) Patent No.: US 12,414,737 B2
(45) Date of Patent: Sep. 16, 2025

(54) IMAGING-BASED REFLEX MEASUREMENTS FOR SEDATION DEPTH MONITORING

(71) Applicant: KONINKLIJKE PHILIPS N.V., Eindhoven (NL)

(72) Inventor: Steffen Weiss, Hamburg (DE)

(73) Assignee: Koninklijke Philips N.V., Eindhoven (NL)

(*) Notice: Subject to any disclaimer, the term of this patent is extended or adjusted under 35 U.S.C. 154(b) by 348 days.

(21) Appl. No.: 17/765,471

(22) PCT Filed: Oct. 1, 2020

(86) PCT No.: PCT/EP2020/077582
§ 371 (c)(1),
(2) Date: Mar. 31, 2022

(87) PCT Pub. No.: WO2021/064134
PCT Pub. Date: Apr. 8, 2021

(65) Prior Publication Data
US 2022/0361809 A1    Nov. 17, 2022

(30) Foreign Application Priority Data
Oct. 3, 2019  (EP) .................................... 19201238

(51) Int. Cl.
*A61B 5/00*    (2006.01)
*A61B 3/11*    (2006.01)
(Continued)

(52) U.S. Cl.
CPC ............ *A61B 5/4821* (2013.01); *A61B 3/112* (2013.01); *A61B 5/004* (2013.01); *A61B 5/0051* (2013.01);
(Continued)

(58) Field of Classification Search
CPC ....... A61B 5/4821; A61B 3/112; A61B 5/004; A61B 5/0051; A61B 5/0057; A61B 5/055;
(Continued)

(56) References Cited

U.S. PATENT DOCUMENTS 6,526,297 B1 * 2/2003 Merilainen .......... A61B 5/0059
                                                              600/472
9,724,538 B2   8/2017 Pekar et al.
(Continued)

FOREIGN PATENT DOCUMENTS

WO    2004060443 A2    7/2004

OTHER PUBLICATIONS

Cohen et al. 1988 Infant Behavior and Development 11:297-304 (Year: 1988).*
(Continued)

*Primary Examiner* — Keith M Raymond
*Assistant Examiner* — Patrick M Mehl (57) ABSTRACT

The present invention relates to sedation assessment. In order to facilitate sedation depth monitoring in an autonomous imaging setting, it is proposed to use the imaging modality itself to measure the response to suitable reflexes in order to determine the depth of sedation wherein suitable reflexes include, but are not limited to, the pupil reflex, so-called superficial reflexes and the withdrawal reflexes. In one embodiment, the pupil reflex may be measured in an MRI system by repeated interleaving of dedicated iris MR imaging with the conventional scan protocol. In another embodiment, superficial reflexes in response to stroking of the skin may be measured. This may involve a dedicated actuator that may be closely integrated with the imaging modality, e.g. an MR receive coil applied to the patient. Alternatively, remote haptic systems may be used. The
(Continued)

reflex is then acquired with a suitable diagnostic imaging method. In another embodiment, the withdrawal reflex in response to pain may be measured. This may involve an actuator that induces sudden stitching pain or very local temperature-induced pain and that is closely integrated with the imaging modality, e.g. a pinching device integrated with a patient support or an MR receive coil applied to the patient. The reflex is then acquired with a suitable diagnostic imaging method.

17 Claims, 5 Drawing Sheets

(51) Int. Cl.
 *A61B 5/055* (2006.01)
 *A61B 6/03* (2006.01)
(52) U.S. Cl.
 CPC ............ *A61B 5/0057* (2013.01); *A61B 5/055* (2013.01); *A61B 6/032* (2013.01)
(58) Field of Classification Search
 CPC ....... A61B 6/032; A61B 3/145; A61B 5/4029; A61B 5/1128; A61B 5/163; A61B 6/501; A61B 6/506; A61B 9/00; A61B 5/1106; A61B 3/11; A61B 3/14; A61B 6/00; A61B 6/037; G08B 6/00
 See application file for complete search history.

(56) References Cited

U.S. PATENT DOCUMENTS

| | | | | |
|---|---|---|---|---|
| 2004/0127954 | A1* | 7/2004 | McDonald, III | A61N 1/36003 607/48 |
| 2006/0058700 | A1* | 3/2006 | Marro | A61B 5/4821 600/554 |
| 2007/0010756 | A1* | 1/2007 | Viertio-Oja | G16H 20/10 600/544 |
| 2007/0203435 | A1* | 8/2007 | Novak | A43B 17/00 601/46 |
| 2012/0226186 | A1 | 9/2012 | Baars et al. | |
| 2015/0011968 | A1 | 1/2015 | Weatherhead | |
| 2016/0045128 | A1 | 2/2016 | Sitt et al. | |
| 2016/0262685 | A1* | 9/2016 | Wagner | A61B 5/1123 |
| 2017/0340681 | A1* | 11/2017 | Lin | A61K 35/744 |
| 2018/0235456 | A1* | 8/2018 | Karakaya | A61B 3/112 |
| 2019/0218255 | A1* | 7/2019 | Chung | A61P 25/00 |

OTHER PUBLICATIONS

Life Science 2010 Manual description IITC Life Science Plantar Test (Hargreaves Method) Mice and Rats) (Year: 2010).*
Ugo Basile SRL (2016 Operating Manual 37450 Dynamic Plantar Aesthesiometer). (Year: 2016).*
M.A. Gray et al "Physiological Recordings: Basic Concepts and Implementation During Functional Magnetic Resonance Imaging" NEUROIMAGE, vol. 47, No. 3, Sep. 1, 2009 p. 1105-1115.
International Search Report and Written Opinion from PCT/EP2020/077582 mailed Feb. 11, 2021.
C. G. Sheahan and D. M. Mathews. "Monitoring and delivery of sedation" British Journal of Anaesthesia 113 (S2): ii37-ii47 (2014). doi:10.1093/bja/aeu378.
Rouche et al. "Evaluation of the depth of sedation in an intensive care unit based on the photo motor reflex variations measured by video pupillometry" Annals of Intensive Care 2013, 3:5.
Shirozu et al. "The effects of anesthetic agents on pupillary function during general anesthesia using the automated infrared quantitative pupilometer" J Clin Monit Comput (2017) 31:291-296.
https://en.wikipedia.org/wiki/List_of_reflexes—downloaded Mar. 22, 2022.
Van Vaals JJ et al. Real-time MR imaging using the LoLo (Local Look) method for interactive and interventional MR at 0.5T and 1.5T. In: Proc of SMR meeting 1994;421.
Caines et al "Comparison of Isoflurane and Propofol for Maintenance of Anesthesia in Dogs with Intracranial Disease Undergoing Magnetic Resonance Imaging" Veterinary Anesthesia and Analgesia 2014 vol. 41, p. 468-479.
Tremoleda et al "Anaesthesia and Physiological Monitoring During in vivo Imaging of Laboratory Rodents: Considerations on Experimental Outcomes and Animal Welfare" EJNMMI Research, 2012.

* cited by examiner

IMAGING-BASED REFLEX MEASUREMENTS FOR SEDATION DEPTH MONITORING

CROSS REFERENCE TO RELATED APPLICATIONS

This application is a U.S. national phase application of International Application No. PCT/EP2020/077582 filed on Oct. 1, 2020, which claims the benefit of EP Application Serial No. 19201238.3 filed on Oct. 3, 2019 and is incorporated herein by reference.

FIELD OF THE INVENTION

The present invention relates to sedation assessment and in particular to a medical imaging system and to a method for assessing a sedation level.

BACKGROUND OF THE INVENTION

Patients under sedation need to be monitored to determine their sedation depth, which is commonly done manually by medical staff. The classical methods to monitor the depth of sedation and General Anesthesia (GA) involve repeated manual monitoring of clinical criteria as responsiveness to verbal and tactile stimulation by staff members.

Automatic monitoring of sedation depth may be desirable in an autonomous imaging setting. Various attempts have been made to find new forms of monitoring that are less manual and more objective, which are criteria as required in autonomous imaging. One of those approaches was to replace the classic manual check of the pupil reflex by video pupillometry with a camera close to the eyes of the patient. Pupillometry is the quantitative measurement of the size of the pupil and its dynamic changes. However, this requires that the patient keeps his/her eyes open, or that the eyes are kept open by some mechanical means. Both is highly inconvenient during longer imaging sessions. It is not expected that any optical or infrared (IR) measurement with devices compatible with autonomous imaging can achieve the required accuracy to measure the pupil diameter through the closed eye lid, because of strong scattering in the lid. In general, any sensor that must be correctly applied to the patient may complicate the workflow and potentially the reliability in autonomous imaging.

SUMMARY OF THE INVENTION

There may be a need to facilitate sedation depth monitoring in autonomous imaging.

The object of the present invention is solved by the subject-matter of the independent claims, wherein further embodiments are incorporated in the dependent claims. It should be noted that the following described aspects of the invention apply also for the medical imaging system and the method for assessing a sedation level.

A first aspect of the present invention relates to a medical imaging system. The medical imaging system comprises a medical imaging apparatus and a sedation assessment apparatus. The medical imaging apparatus is configured to acquire a sequence of images of a body part of a patient to detect a response reaction of at least one reflex of the patient. The at least one reflex is selected from reflexes with a response reaction that is in dependence on a sedation depth. The sedation assessment apparatus is configured to determine, based on the detected response reaction, a sedation level of the patient.

In other words, it is proposed to use the imaging modality itself to measure the response to suitable reflexes in order to determine the depth of sedation. As previously mentioned, if an additional sensor is used to measure the response to suitable reflexes, the sensor may have to be correctly applied to the patient. This may complicate the workflow and potentially the reliability in autonomous imaging. Hence, using the imaging modality itself without using an additional sensor to measure the response to suitable reflexes may facilitate the workflow and improve the reliability in autonomous imaging.

The medical imaging apparatus as used herein refers to a device for acquiring the internal structure of an object as an image. The medical imaging apparatus is a non-invasive examination device that captures and processes structural details, internal tissues, and/or fluid flow in the body. A user, such as a doctor, can diagnose a health condition and a disease of a patient by using a medical image outputted from a medical imaging apparatus. The medical imaging apparatus may include e.g. magnetic resonance imaging (MM) devices, computed tomography (CT) devices, and X-ray devices.

The human body is provided with about fifty reflexes covering a wide range of body systems, but only some reflexes may be suitable for sedation monitoring in an autonomous imaging setting, because they have to meet at least the following two criteria: (1) The response reaction of the reflex must depend on sedation depth; and (2) the response must be measurable in the clinical setting such that it can be easily integrated with diagnostic imaging. In other words, for diagnostic purposes, the medical imaging apparatus (e.g. MRI, CT, or X-ray device) is used to image the body to obtain a correct diagnosis and determine future care. The reflexes should be selected to have a patient reaction that is measurable by the medical imaging apparatus in a clinical setting. Thus, during diagnostic medical imaging, the imaging modality itself, i.e. the medical imaging apparatus, can be directly used to measure the response to suitable reflexes without using an additional sensor.

Many reflexes as the well-known patella or knee-jerk reflex are monosynaptic, which means that their reflex arc involves only two neurons including one sensory neuron and one reacting motor neuron connected by a single synapse typically in the spine. Because this pathway does not include the central nervous system (CNS), the reaction does not depend on the status of the CNS and hence not on sedation depth. Further monosynaptic reflexes are biceps reflex, brachioradialis reflex, extensor digitorum reflex, triceps reflex, and achilles reflex. All those motor reflexes protect muscles or tendons from overstretching. Other reflexes are not suitable because they involve stimuli or reactions inconvenient for the patient or involve major body motion like the cough, the sneeze reflex, or the eye blink reflex upon touching the eye. There are also reflexes that are unsuitable because they address internal physiological quantities, which are not easy to measure as the baroreflex, the Bainbridge reflex, the Bezold-Jarisch reflex.

The following reflexes may be suitable for sedation monitoring in autonomous imaging.

The pupil reflex in response to changes of illumination of the retina may be suitable for sedation depth measurement as detailed out below. The pupil reflex may be suitable for sedation depth monitoring in a magnetic resonance imaging (MM) system. For example, the pupil reflex may be measured in an MRI system by repeated interleaving of dedicated iris MR imaging with the conventional scan protocol.

Another group of suitable reflexes includes the superficial reflexes, which have motor responses in response to scraping of the skin. Examples include the abdominal reflex, the cremaster reflex, the glabellar reflex and the normal plantar response. The latter involves flexing of the big toe upon stroking of the sole of the foot and may be particularly useful, because it involves gentle stimulation and a response with minor local motion. The glabellar reflex, also known as the "glabellar tap sign", involves eye blinking upon repetitive tapping on the forehead and seems similarly useful. The superficial reflexes may be suitable for sedation depth monitoring in an MRI system, in an X-ray imaging system, or in a computed tomography (CT) system. The MR imaging apparatus, the X-ray imaging apparatus, or the CT imaging apparatus may acquire a sequence of images of a body part to detect the response reaction, e.g., minor local motion, eye blinking, etc.

Another suitable group includes withdrawal reflexes of limbs or fingers because they can be easily stimulated and measured during diagnostic imaging if induced motion does not disturb imaging. The withdrawal reflexes may be suitable for sedation depth monitoring in an MRI system, in an X-ray imaging system, or in a CT system. These systems may acquire a sequence of images of a body part to detect the response reaction, i.e., the induced motion of limbs or fingers.

According to an embodiment of the present invention, the at least one reflex comprises a pupil reflex.

Several different types of measures may be used for determining the pupil reflex including, but not limited to, resting pupil size (MAX), minimum pupil size after light stimulation (MIN), ratio of pupil size reduction ([MAX-MIN]/MAX expressed as a percentage), latency duration (i.e., time between initiation of retinal light stimulation and onset of pupillary constriction), constriction velocity (i.e., extent of constriction/duration of constriction), maximum constriction velocity, and dilation velocity (i.e., extent of pupil size recovery/duration of recovery).

According to an embodiment of the present invention, the medical imaging apparatus is configured to detect a resting size of an iris of the patient for measuring the pupil reflex.

The resting pupil size (MAX) correlates well with sedation depth for common agents, such as sevoflurane-remifentanil (SEV/REM), sevoflurane (SEV), desflurane-remifentanil (DES/REM), and propofol-remifentanil (PRO/REM)). The resting pupil size (MAX) shows a large response and does not require any stimulus. The typical time scales on which the depth of sedation changes are in the order of few minutes. High resolution MR imaging may be applied to measure the resting size of the iris to provide a measure of sedation depth. The size of the pupil changes in the order of millimeters, which can be resolved with MR imaging methods.

According to an embodiment of the present invention, the medical imaging apparatus comprises a magnetic resonance imaging, MRI, apparatus.

According to an embodiment of the present invention, the MR imaging apparatus is configured to apply a dedicated sequence for performing pupillometry.

Conventional MR imaging of the eye performed for oncology may be used to measure the pupil reflex, which can deliver high-resolution detail. However, such method may require imaging times in the order of several minutes. Here, a dedicated sequence may be preferred that only has the purpose to perform pupillometry and is thus much quicker.

According to an embodiment of the present invention, the dedicated sequence is a T2w-turbo spin echo sequence that uses slice-selective refocussing pulses in a phase encoding direction.

A variant of a T2w-turbo spin echo sequence may be applied that uses slice-selective refocussing pulses in phase encoding direction. This limits the field of view to the eye region and will therefore enable a 1 mm in-plane resolution in an imaging time in less than one minute. A fixed size of the field of view may be used for all patients because inter-subject variation of the size of the human eye is very small. Eye motion may complicate the imaging process, but there are many approaches known for motion reduction and motion compensation known in MRI, which can be applied to mitigate this effect.

According to an embodiment of the present invention, the at least one reflex comprises at least one of a superficial reflex and a withdrawal reflex.

According to an embodiment of the present invention, the medical imaging system further comprises at least one stimulus generator. The at least one stimulus generator is configured to generate at least one stimulus at an impact region on a patient's skin to stimulate a response reaction of the at least one reflex.

In an example, the at least one stimulus generator may comprise a remote haptic device configured to, from a distance, without contacting the patient, stimulate a response reaction of the patient.

In another example, the at least one stimulus generator may comprise a wearable device, such as a heating device attachable to the patient, to stimulate a response reaction of the patient.

In a further example, the at least one stimulus generator may comprise an actuator that may be closely integrated with the imaging modality, e.g., a pinching device integrated with a patient support or an MR receive coil applied to the patient.

The at least one stimulus generator may be controlled by a controlling device to stimulate a response reaction of at least one reflex at a desired intensity, repetition rate, and/or duration. The controlling device may send a control signal to the at least one stimulus generator to control the intensity, repetition rate, and/or duration of the stimulation. The control signal may be sent via a physical cable, e.g., Universal Serial Bus (USB) cable, or wirelessly, e.g., Bluetooth or wireless LAN (WiFi). In one example, the control signal may be generated in response to the commands from a user interface. In another example, the control signal may be generated automatically by using the machine learning and statistical techniques on the historical data of multiple patients.

According to an embodiment of the present invention, the superficial reflex comprises at least one of a normal plantar response and a glabellar reflex.

According to an embodiment of the present invention, the at least one stimulus generator comprises at least one of the following devices to stimulate the normal plantar response: a stroking device that is attachable to a sole of a foot of the patient, and a remote haptic device configured to induce, from a distance, a haptic sensation at an impact region on a sole of a foot of the patient.

An exemplary example of the remote haptic device, i.e., remote haptic device 130a, is illustrated in FIG. 1.

According to an embodiment of the present invention, the at least one stimulus generator comprises at least one of the following devices to stimulate the glabellar reflex: a device configured to repetitive tap on a forehead of the patient, and a remote haptic device configured to induce, from a distance, a haptic sensation at an impact region on a forehead of the patient.

Figure 1A:
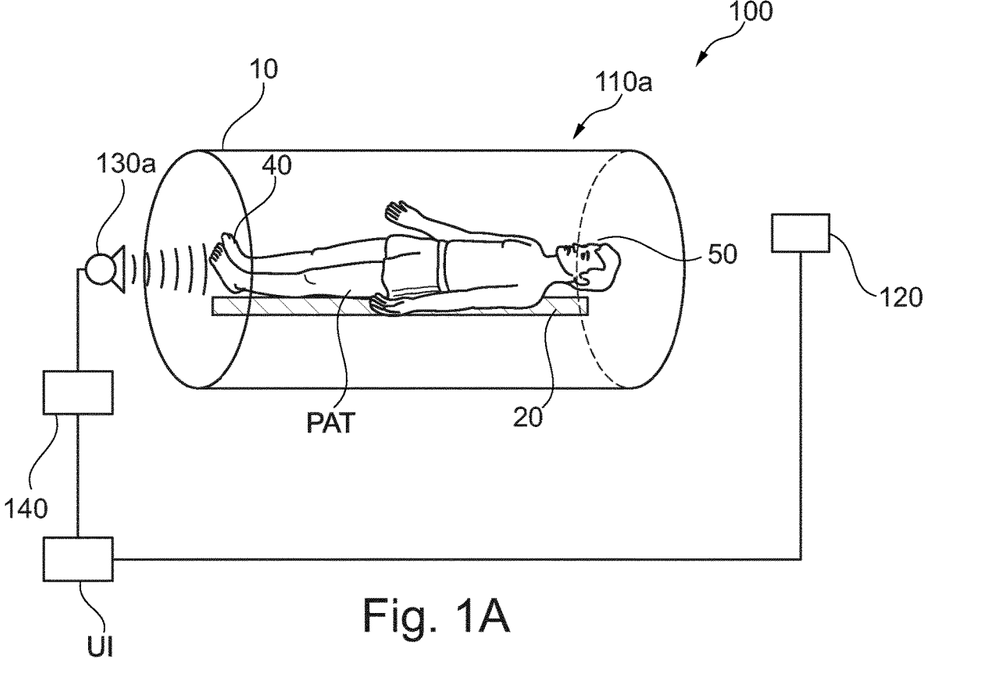
Figure 1B:
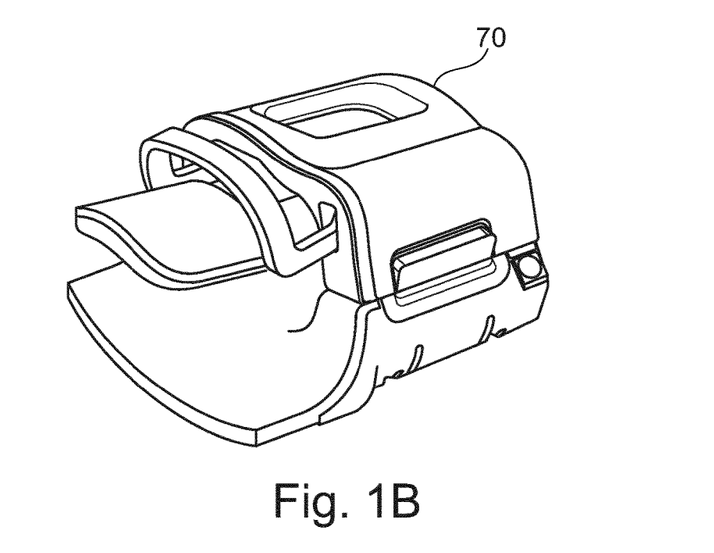
FIG. 1B schematically shows an example of an MR head coil.

For example, the device may be integrated with an MR head coil 70 as illustrated in FIG. 1B.

According to an embodiment of the present invention, the remote haptic device comprises at least one of the following transmitters:
i) a mid-air acoustic transmitter;
ii) mid-air ultrasound haptic transmitter;
iii) an air nozzle;
iv) an electromagnetic wave transmitter;
v) an electric transmitter;
vi) a magnetic transmitter; and
vii) a radio-frequency transmitter.

The mid-air acoustic transmitter uses acoustic waves to create acoustic radiation pressure, which is capable of inducing a haptic sensation at any desired intensity, frequency, and/or duration. For example, by modulating an acoustic field at the range of haptic sensitivity e.g. 10-200 Hz the sound is perceived as vibration.

The mid-air ultrasound haptic transmitter may form an ultrasound beam being formed at a specific focal point and create an acoustic radiation pressure. The focused ultrasound waves cause, at a distance and in a non-invasive manner, touch sensation at any desired intensity, frequency, and/or duration.

The air nozzle may create an airflow pattern that gives rise to a jet of directed air capable of inducing the haptic sensation on the patient's skin at the impact region. Either direct compressed air methods or vortex-based methods may be used to simulate the tactile sensation.

The electromagnetic wave transmitter, such as laser light, may be used to create a haptic effect at a distance from the source of excitation. The electromagnetic wave transmitters may be a pulsed laser based system, such as nanosecond laser, which, when applied to the skin evokes tactile sensation. For example, the electromagnetic radiation is configured to excite mechanoreceptors embedded in the patient's skin. For example, the nudging transmitter may be arranged as a laser transmitter operable at a suitable frequency.

The mentioned transmitters may be used singly or in combination. For example, the nudging signal may be pulsed. In any of the above mentioned embodiments, the frequency of the single, the frequency of the pulses and/or intensity of the nudging signal may be held constant throughout the nudging operation but may also vary in other embodiments. In more detail, the intensity of the nudging signal may drop the closer the region of interest is to the target area. Proximity information may in addition or instead be modulated by varying a frequency of the pulsation of the nudging signal. In a similar manner the frequency of the ultrasound signal itself may be changed.

According to an embodiment of the present invention, the at least one stimulus generator is configured to induce a sudden stitching pain and/or a local temperature-induced pain at an impact region on the patient's skin to stimulate the withdrawal reflex.

In an example, the at least one stimulus generator may comprise an actuator that may be closely integrated with the imaging modality, e.g., a pinching device integrated with a patient support or an MR receive coil applied to the patient.

Figure 5:
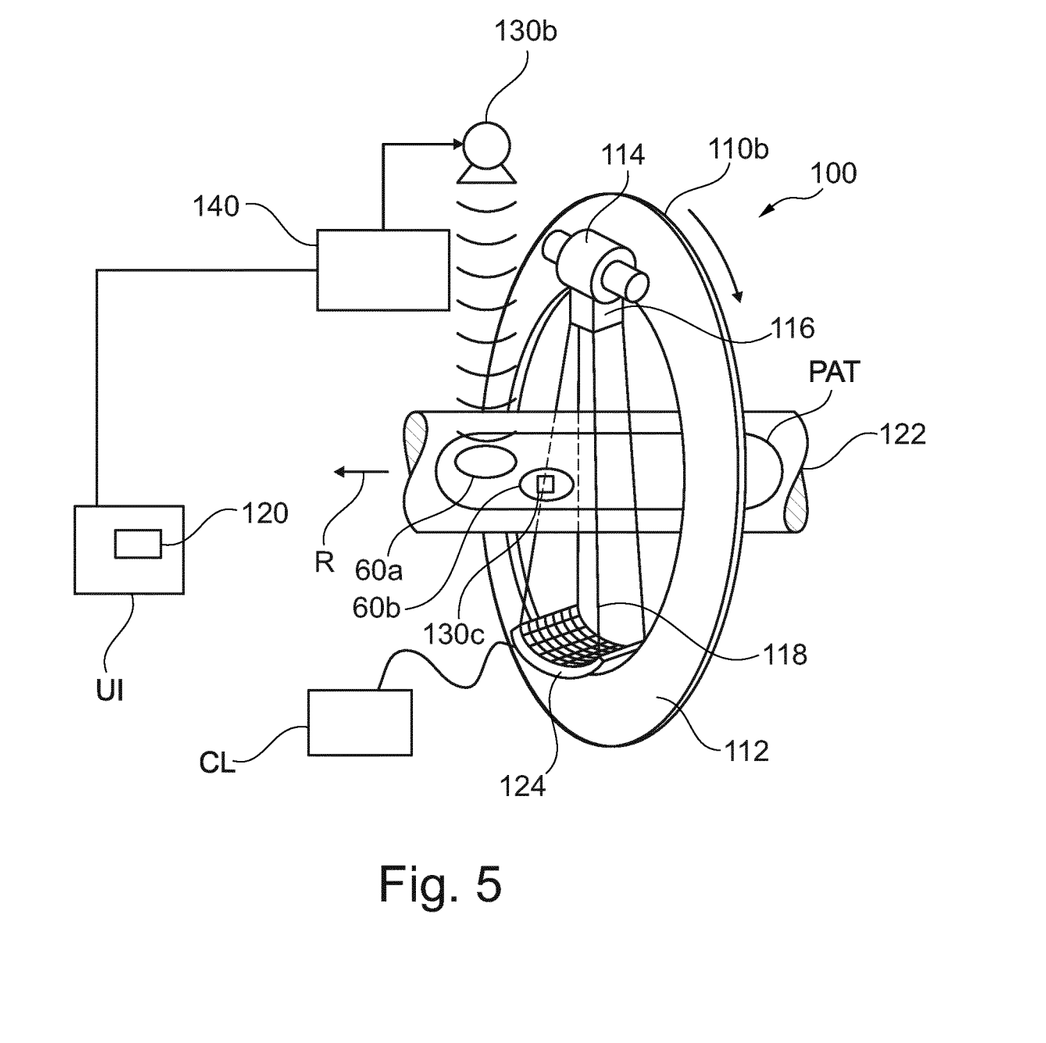
FIG. 5 schematically shows another medical imaging system according to some embodiments of the present disclosure.

In a further example, the at least one stimulus generator may comprise a heating and/or cooling device that may be attachable to an impact region on the patient's skin and configured to heat or cool this impact region for inducing a pain sensation. An exemplary example of the heating and/or cooling device, i.e., device 130c, is illustrated in FIG. 5.

According to an embodiment of the present invention, the medical imaging apparatus comprises at least one of the following: an MR imaging apparatus, an X-ray imaging apparatus, and a computed tomography, CT, imaging apparatus.

The MR imaging apparatus may be configured to apply a dedicated sequence to acquire images of a body part of a patient to detect a response reaction of at least one reflex of the patient. This will be explained hereafter and particularly with respect to the exemplary example in FIG. 1A.

The X-ray imaging apparatus and the CT imaging apparatus may be configured to acquire a sequence of low-resolution scout images of a body part of a patient to detect a response reaction of at least one reflex of the patient. The CT imaging apparatus may also comprise a positron emission tomography-computed tomography (PET-CT) imaging apparatus or a single-photon emission computed tomography-computed tomography (PET-CT) imaging apparatus. This will be explained hereafter and particularly with respect to the exemplary example in FIG. 5.

A second aspect of the present invention relates to a method for assessing a sedation level. The method comprises:
    acquiring, with a medical imaging apparatus, a sequence of images of a body part of a patient to detect a response reaction of at least one reflex of the patient;
        wherein the at least one reflex is selected from reflexes with a response reaction that is in dependence on a sedation depth; and
    determining, based on the detected response reaction, a sedation level of the patient.

A third aspect of the present invention relates to a computer program element, which, when being executed by at least one processing unit, is adapted to cause the processing unit to perform the above and below described method.

A fourth aspect of the present invention relates to a computer readable medium stored on the program element.

These and other aspects of the present invention will become apparent from and be elucidated with reference to the embodiments described hereinafter.

Definitions

The term "user" as used herein shall be understood as medical personnel at least partly involved in an administrative or organizational manner in the imaging procedure.

The term "patient" as used herein shall be seen as a person, or in veterinary settings, an animal (in particular a mammal), who is imaged.

BRIEF DESCRIPTION OF THE DRAWINGS

These and other aspects of the invention will be apparent from and elucidated further with reference to the embodiments described by way of examples in the following description and with reference to the accompanying drawings, in which FIG. 1A schematically shows a medical imaging system according to some embodiments of the present disclosure.

It should be noted that the figures are purely diagrammatic and not drawn to scale. In the figures, elements which correspond to elements already described may have the same reference numerals. Examples, embodiments, and optional features, whether indicated as non-limiting or not, are not to be understood as limiting the invention as claimed.

DETAILED DESCRIPTION OF EMBODIMENTS

FIG. 1A shows schematically and exemplarily an embodiment of a medical imaging system 100. The medical imaging system 100 comprises a medical imaging apparatus 110, such as a MR imaging apparatus 110a in FIG. 1A and a CT imaging apparatus 110b in FIG. 5, and a sedation assessment apparatus 120. The medical imaging apparatus may be any one of i) an MR imaging apparatus, ii) an X-ray imaging apparatus, and iii) a CT imaging apparatus. The CT imaging apparatus may be a PET-CT imaging apparatus or a SPET-CT imaging apparatus.

In this exemplary embodiment in FIG. 1A, the medical imaging apparatus 10 is an MR imaging apparatus 110a with an MR bore 10 and a patient support table 20. According to FIG. 1A, a patient PAT, which may be a human patient as illustrated in FIG. 1A or an animal (not shown), is placed on top of the patient support table 20, which in an operable condition of the system 100 is arranged within the MR bore 10.

Sedation quantification is an important area in scan disruptive events. It is required to give optimal sedation dosage to the patients. In order to determine a sedation level of the patient PAT within the MR bore 10, the medical imaging apparatus 110 is configured to acquire a sequence of images of a body part of the patient PAT to detect a response reaction of at least one reflex of the patient.

As previously mentioned, the human body is provided with about fifty reflexes covering a wide range of body systems, but only some reflexes are suitable for sedation monitoring in an autonomous imaging setting, because they have to meet at least two criteria: (i) The at least one reflex is selected from reflexes that have a response reaction in dependence on a sedation depth; and (ii) the response reaction is measurable in a clinical setting such that it can be integrated with diagnostic imaging.

Reflexes that are suitable for sedation monitoring in the exemplary MR imaging system in FIG. 1A include at least one of a pupil reflex, a superficial reflex, and a withdrawal reflex.

In the first example, the pupil reflex may be measured in an MRI system based on at least one of the following: resting pupil size (MAX), minimum pupil size after light stimulation (MIN), ratio of pupil size reduction ([MAX-MIN]/MAX), latency duration, constriction velocity, maximum constriction velocity, and dilation velocity. For some measures in the list, the temporal resolution of MR imaging may not sufficient to resolve the dynamic quantities.

Figure 2:
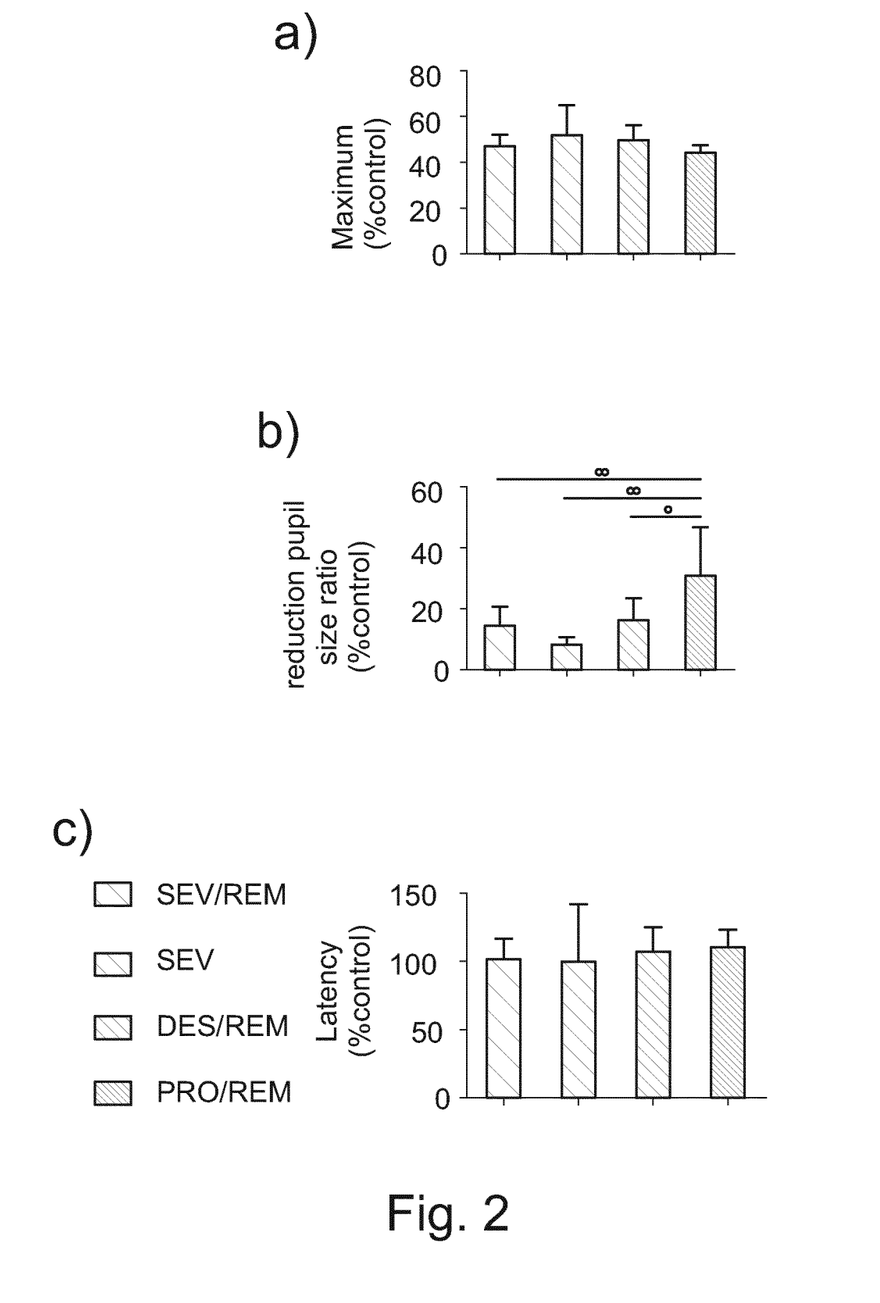
FIGS. 2A to 2C show the response of three different pupil measurements to the administration of different sedation agents including SEV/REM, SEV, DES/REM, PRO/REM.

It is known and has also been shown for video-pupillometry that the resting pupil size (MAX) correlates well with sedation depth for common agents, such as SEV/REM, SEV, DES/REM, and PRO/REM. For example, FIGS. 2A to 2C illustrate the response of three different pupil measurements to the administration of different sedation agents including SEV/REM, SEV, DES/REM, PRO/REM. In particular, FIG. 2A illustrates the resting pupil size (MAX) in comparison to non-sedated control group. FIG. 2B illustrates the reduction of the pupil size after a light stimulus. FIG. 2C illustrates the increase of latency of the pupil reflex in comparison to non-sedated patient group. It should be noted that the resting pupil size (MAX) shows a large response and does not require any stimulus. The typical time scales on which the depth of sedation changes are in the order of few minutes. It is therefore proposed to apply high resolution MR imaging to measure the resting size of the iris to provide a measure of sedation depth. The size of the pupil changes in the order of millimeters, which can be resolved with MR imaging methods.

Figure 3:
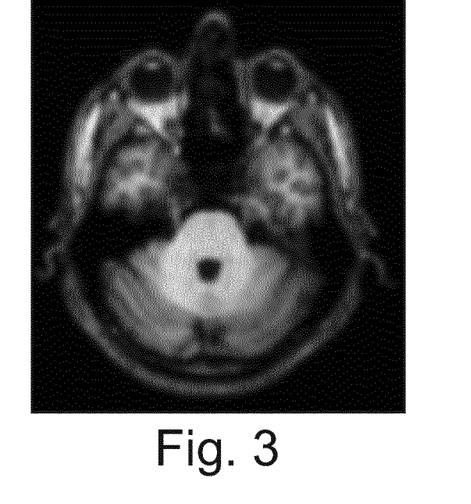
FIG. 3 shows an example of a low-resolution scout image for automated scan planning.

For automated scan planning, the position of the eye and the approximate position of the eye lens may be determined already on scout MR images as used at the beginning of during every imaging session. It is proposed to determine the position of the eye and lens with such a scan automatically and then plan a more highly resolved iris scan. Preferably, the iris scan is planned in coronal orientation coplanar with the iris, which is known to be in front of the lens. Auto planning may be performed with known auto-planning concepts similar to Philips SmartExam™ in brain, where a low-resolution scout image is acquired, automated recognition of patient-specific anatomical landmarks is carried out, and the orientation of slices in the diagnostic scan is estimated based on the identified landmarks. For a detailed discussion concerning the above-mentioned auto-planning concepts for Philips SmartExam™ in brain, reference is made to the following patent U.S. Pat. No. 9,724,538 B2. An example of the low-resolution scout image for automated scan planning is illustrated in FIG. 3. In FIG. 3, a transverse T1w MR scout image though the eyes is illustrated, which is typically acquired in 2 seconds. The eye lens is depicted as a white spot within the frontal part of the black eye ball. Such a scan may be proposed to determine the approximate position of the eye lens and to plan a coronal scan coplanar with the iris located in just front of the lens.

Conventional MR imaging of the eye performed for oncology may be used to measure the pupil reflex, which can deliver high resolution detail. However, such method may require imaging times in the order of several minutes. Here, a dedicated sequence may be preferred that only has the purpose to perform pupillometry and is thus much quicker.

Preferably, a variant of a T2w-turbo spin echo sequence may be used that uses slice-selective refocussing pulses in phase encoding direction. This limits the field of view to the eye region and will therefore enable a 1 mm in-plane resolution in an imaging time in less than one minute. A fixed size of the field of view may be used for all patients because inter-subject variation of the size of the human eye is very small. Eye motion may complicate the imaging process, but there are many approaches known for motion reduction and motion compensation known in MRI which can be applied to mitigate this effect.

Figure 4:
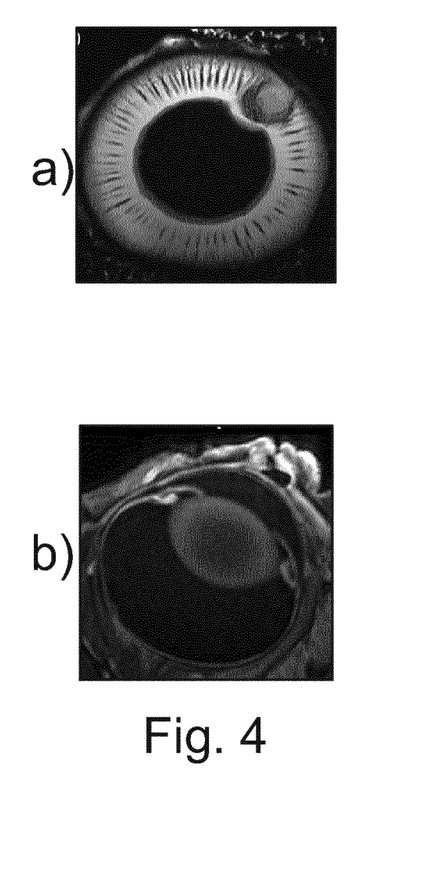
FIGS. 4A and 4B show high-resolution MR imaging of the human eye.

FIGS. 4A and 4B illustrate high-resolution MR imaging of the human eye. In particular, FIG. 4A illustrates a T2w image of a slice oriented coplanar with the iris. It contains a pathological lesion at 2 o'clock. FIG. 4B illustrates a T1w image oriented perpendicular to this, again depicting the glass body (black), the eye lens (grey), and the lobes of the iris lying on top of the lens.

Once the response reaction of the pupil reflex is detected, the sedation assessment apparatus 120 is configured to determine, based on the detect response reaction, a sedation level of the patient PAT. The sedation determination apparatus 120 may be part of, or include an Application Specific Integrated Circuit (ASIC), an electronic circuit, a processor (shared, dedicated, or group) and/or memory (shared, dedicated, or group) that execute one or more software or firmware programs, a combinational logical circuit, and/or other suitable components that provide the described functionality. In an example, the sedation assessment apparatus 120 may use any appropriate set of image processing methods to evaluate the pupil diameter. The basic task is to find a circle with approximately constant image intensity and located approximately centrally in the image and to determine its radius. This may be achieved with a model-based segmentation method, e.g. modelling the pupil as circle with following fit parameters: x and y-position of the pupil center in the iris image, pupil radius, mean image intensity of pupil. The model parameters may be constrained to common dimensions and image intensities.

In the second example, superficial reflexes in response to stroking of the skin may be measured. The superficial reflex comprises at least one of a normal plantar response and a glabellar reflex.

In order to stimulate a response reaction of the superficial reflexes, the medical imaging system may further comprise at least one stimulus generator 130, such as a remote haptic device 130a as illustrated in FIG. 1. The at least one stimulus generator 130 is configured to generate at least one stimulus at an impact region on a patient's skin to stimulate a response reaction of the at least one reflex.

The at least one stimulus generator 130 may comprise at least one of the following devices to stimulate the normal plantar response: a stroking device that is attachable to a sole of a foot of the patient and a remote haptic device configured to induce, from a distance, a haptic sensation at an impact region on a sole of a foot of the patient.

In the exemplary example in FIG. 1A, a remote haptic device 130a is configured to induce, from a distance, without physical contact with the patient PAT, a haptic sensation at an impact region on a sole of a foot 40 of the patient PAT to stimulate the normal plantar response. The remote haptic device 130a may be mounted within the imaging room or at or inside the MR bore 10. Examples for causing such haptic sensation may include i) a mid-air acoustic transmitter, ii) a mid-air ultrasound haptic transmitter, iii) an air nozzle, iv) an electromagnetic wave transmitter, v) an electric transmitter, vi) a magnetic transmitter, and vii) a radio-frequency transmitter.

The remote haptic device 130a may create single or multiple remote nudges with one or more transmitters at different intensities, repeat rates, and/or durations for inducing one or more different haptic sensations. The patient reactions to the one or more different haptic sensations could be any known response of a sedated patient to a conventional physical nudge, e.g., flexion of toes, which can be detected by the MR imaging system.

Taking an ultrasound based haptic system as an example, the remote haptic device 130a may comprise one or more mid-air ultrasound haptic transmitters (not shown) configured to cause a directed or focused ultrasound beam, which can be directed to the desired impact region on the patient's body. The mid-air ultrasound haptic transmitters may create an acoustic interference pattern that gives rise to the directed ultrasound beam capable of inducting the haptic sensation on the patient's skin at the impact region. The focused ultrasound waves cause, at a distance and in a non-invasive manner, touch sensation at any desired intensity, frequency, and/or duration. In some embodiments, the acoustic field created by a phased array may allow forming volumetric acoustic fields, such as a palpable sphere or other geometrical configurations. The direction of the ultrasound beam may be automatically or manually adjustable to impact a desired impact region. When applied to the patient at the impact region, the patient then experiences a sensation as if a physical object of the specified shape is in skin contact. It is not necessary for the patient to expose bare skin for this, because ultrasound waves are capable of coupling-in onto the skin through a suitable thin garment such as hospital gowns usually wore by patients.

Of course, other types of transmitters may also be used instead of or in additional to the mid-air ultrasound haptic transmitters. For example, in some embodiments one or more air nozzles may be used to create an airflow pattern that gives rise to a jet of directed air capable of inducing the haptic sensation on the patient's skin at the impact region. Either direct compressed air methods or vortex-based methods may be used to simulate the tactile sensation. In another example, one or more electromagnetic wave transmitters, such as laser light, may be used to create a haptic effect at a distance from the source of excitation. The electromagnetic wave transmitters may be a pulsed laser based system, such as nanosecond laser, which, when applied to the skin evokes tactile sensation. In some embodiments, heat radiation may be used as certain receptors, e.g., TRPV1, in human skin respond not only to heat but also to pain. By eliciting both responses in turn, a haptic sensation can be caused. This may be achieved by controlling a heat source, such as a halogen lamp or other. The heat source is suitably focused using one or more reflectors and the focus is rapidly switched. The above-mentioned transmitter embodiments may be used singly or in combination or in any sub-combination.

The patient reaction, such as flexion of toes, may be detected by the MR imaging apparatus by capturing a sequence of images of the toes. The sedation assessment apparatus may use any appropriate set of image processing methods to evaluate the response reaction, e.g., induced motion of the stimulated body part, and determine, based on the detected response reaction, a sedation level of the patient.

Alternatively or additionally, the at least one stimulus generator 130 may be a stoking device (not shown) that is attachable to the sole of the foot of the patient to stimulate the normal plantar response.

Similarly, the at least one stimulus generator 130 may comprise at least one of the following devices to stimulate the glabellar reflex: a device configured to repetitive tap on a forehead of the patient, and a remote haptic device configured to induce, from a distance, a haptic sensation at an impact region on a forehead of the patient.

In the exemplary example in FIG. 1A, the glabellar reflex may be stimulated by a dedicated device (not shown) that may be integrated with an MR head coil 70. An example of the MR head coil 70 is illustrated in FIG. 1B. The MR head coil 70 may be integrated in the patient support table 20 and attachable to the patient's head. Alternatively or additionally, a remote haptic device (not shown) may be provided to induce, from a distance, without physical contact with the patient PAT, a haptic sensation at an impact region on a forehead 50 of the patient PAT. The remote haptic device may be mounted within the imaging room or at or inside the MR bore 10. In some examples, the remote haptic device, e.g., an air nozzle, may be integrated with the MR head coil 70 as illustrated in FIG. 1B to create an airflow pattern that gives rise to a jet of directed air capable of inducing the haptic sensation on the patient's forehead.

In the third example, withdrawal reflexes in response to pain may be measured. This may involve the at least one stimulus generator that induces sudden stitching pain or very local temperature-induced pain at an impact region on the patient's skin to stimulate the withdrawal reflex. Preferably, the at least one stimulus generator may be closely integrated with the imaging modality, e.g. a pinching device integrated with a patient support or an MR receive coil applied to the patient. The reflex is then acquired with the MR imaging apparatus 110a.

Optionally, the medical imaging system 100 may further comprise a controlling device 140. The controlling device 140 may be configured to generate a control signal to control the at least one stimulus generator to stimulate a response reaction of at least one reflexes. The control signal may be transmitted via a physical cable or wirelessly.

In the exemplary example in FIG. 1A, the controlling device 140 is configured to generate a control signal to control the remote haptic device 130a to induce desirable haptic sensations. For example, the control signal may be used to control an intensity, a repetition rate, and/or a duration of the haptic sensation at a particular impact region on the patient's skin. In some examples, the controlling device 140 may be configured to generate the control signal in response to an input request received from a user interface UI. For example, at least one or a combination of an intensity, a repetition rate and/or a duration may be configured in response to commands received from the user interface UI. Examples of the user interface UI may include, but not limited to, a touch screen, a keystroke based interface, and a joystick arrangement. The user interface UI is preferably arranged remotely away from the imaging apparatus, for instance outside the imaging room. Alternatively, the user interface UI may be arranged inside the room. The user interface may configured to allow remote controlling of the controlling device and/or remote monitoring the detected patient reaction and/or the determined sedation level. For example, some information may be sent remotely for further evaluation by an anesthetist. The information shared to a remote person may be the haptic touch or the evaluation of the patient reaction. If the stimulus generator comprises a plurality of transmitters, such as a plurality of mid-air ultrasound transmitters, the user interface UI may include user interface elements that allow the user to select and switch between different transmitters to induce haptic/pain sensation at different impact regions to induce superficial reflexes and/or withdrawal reflexes. For example, in the exemplary example in FIG. 1A, the user may select to switch between the remote haptic device 130a and the dedicated device to stimulate the normal plantar response or the glabellar reflex.

However, in other embodiments, the controlling device may control the at least one stimulus generator automatically. In particular, the controlling device 140 may be configured to change any one or all of the direction and modulation of the nudging signal based on historical data of the patients. For example, by using the machine learning and statistical techniques on the historical data of multiple patients, it may be defined a sequence of nudge intensity with different gradients for sensitivity control.

In the exemplary example in FIG. 1A, the sedation assessment apparatus 120 is an individual computing device. However, in some examples, the sedation assessment apparatus 120 may be part of the user interface UI, such as the exemplary example illustrated in FIG. 5.

FIG. 5 shows schematically and exemplarily another embodiment of a medical imaging system 100. In this exemplary embodiment, the medical imaging apparatus 110 is a CT scanner 110b. The CT scanner 110b comprises a gantry 112, which is capable of rotation about a rotational axis R that extends parallel to a z direction. A radiation source 114, which in this embodiment is an x-ray tube, is mounted on the gantry 112 and is provided with a collimator 116, which forms a conical radiation beam 118 from the radiation generated by the radiation source 114. The radiation traverses a human patient PAT within a cylindrical examination zone 122. After having traversed the examination zone 122 and hence the patient PAT the radiation beam 118 is incident on a detection device 124 which comprises a two-dimensional detection surface. In addition, the detection device 124 is mounted on the gantry 112. The control logic CL is configured to generate a scan protocol inducing the medical imaging apparatus 110b, in this embodiment, a CT scanner, to perform a medical scan of a body part of the patient PAT. Further examples of the CT scanner include PET-CT scanner and SPECT-CT scanners.

Reflexes that are suitable for sedation monitoring in the exemplary CT scanner in FIG. 5 include at least one of a superficial reflex and a withdrawal reflex.

In a first example, superficial reflexes in response to stroking of the skin may be measured. The superficial reflex comprises at least one of a normal plantar response and a glabellar reflex.

In order to stimulate a response reaction of the superficial reflexes, the medical imaging system 100 may further comprise at least one stimulus generator 130, such as a remote haptic device 130b as illustrated in FIG. 5. The at least one stimulus generator 130 is configured to generate at least one stimulus at an impact region 60a on a patient's skin to stimulate a response reaction of the at least one reflex. The remote haptic device 130b may be mounted within the imaging room or at or inside the cylindrical examination zone 122. Examples for causing such haptic sensation may include i) a mid-air acoustic transmitter, ii) a mid-air ultrasound haptic transmitter, iii) an air nozzle, iv) an electromagnetic wave transmitter, v) an electric transmitter, vi) a magnetic transmitter, and vii) a radio-frequency transmitter. In an example, the remote haptic device 130b may be arranged and configured to induce, from a distance, without physical contact with the patient, a haptic sensation at an impact region on a sole of a foot of the patient PAT to stimulate a plantar response. In another example, the remote haptic device 130b may be arranged and configured to induce, from a distance, without physical contact with the patient, a haptic sensation at an impact region on a forehead of the patient PAT to stimulate a glabellar reflex.

Alternatively or additionally, a stroking device that is attachable to a sole of a foot of the patient may be used to stimulate the normal plantar response. A device configured to repetitive tap on a forehead of the patient may be used to stimulate the glabellar reflex.

In a second example, withdrawal reflexes in response to pain may be measured. This may involve the at least one stimulus generator that induces sudden stitching pain or very local temperature-induced pain at an impact region on the patient's skin to stimulate the withdrawal reflex. For example, the at least one stimulus generator may be closely integrated with the imaging modality, e.g., a pinching device integrated with a patient support or an MR receive coil applied to the patient. In the exemplary example in FIG. 5, the at least one stimulus generator 130 may comprise a heating and/or cooling device 130c, which is attachable to an impact region 60b on the patient's skin and configured to heat or cool this impact region 60b for inducing a pain sensation. In other words, the at least one stimulus generator may be a wearable device.

The response reaction of the superficial reflexes and the withdrawal reflexes may induce motion of one or more body parts of the patient. For example, in healthy adults, the plantar reflex may cause a downward response of the toes. For example, the withdrawal reflex may cause an induced motion of limbs or fingers. The CT scanner 110b may thus be configured to acquire a sequence of images of at least one of these body parts to detect the induced motion. The sedation assessment apparatus 120 then determines, based on the detected response reaction, e.g., induced motion of a body part of the patient, a sedation level of the patient.

Optionally, the medical imaging system 100 may further comprise a controlling device 140, which may be configured to generate a control signal to control the at least one stimulus generator to stimulate a response reaction of at least one reflexes. The control signal may be transmitted via a physical cable or wirelessly.

In the exemplary example in FIG. 5, the controlling device 140 is configured to generate a control signal to control the remote haptic device 130b to induce desirable haptic sensations. The controlling device 140 may also be configured to generate a control signal to control the heating and/or cooling device 130c to stimulate the response reaction of the withdrawal reflex.

The controlling device 140 may be controlled by a user interface UI. For example, the control signal may be generated in response to the commands received from the user interface UI. In some examples, the user interface UI may be a computing device, e.g., a personal computer (PC). The sedation assessment apparatus 120 may be part of the user interface UI.

Figure 6:
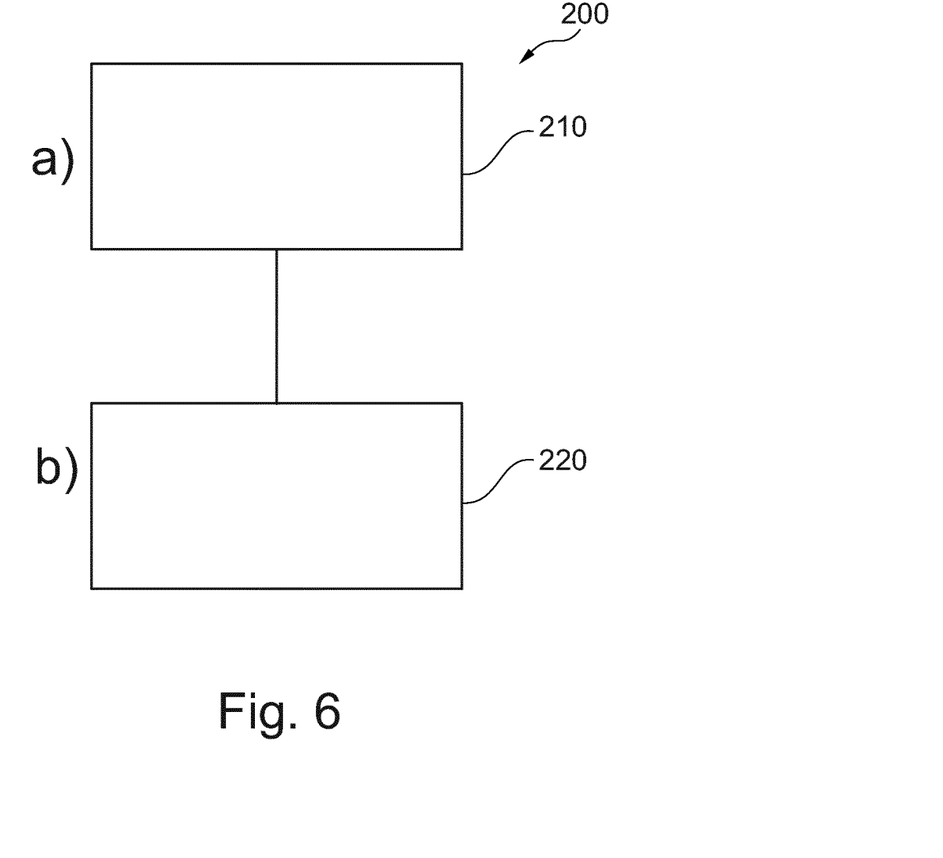
FIG. 6 shows a flow chart of a method to assess a sedation level.

Reference is now made to FIG. 6 that shows a flow diagram of a method 200 for assessing a sedation level. Although the below described steps relate to the above described system these steps are not necessarily tied to the described system and the below described method for assessing a sedation level may also be understood as a teaching in their own right.

In step 210, a medical imaging apparatus acquires a sequence of images of a body part of a patient to detect a response reaction of at least one reflex of the patient. The at least one reflex is selected from reflexes with a response reaction that is in dependence on a sedation depth. The medical imaging apparatus may be at least one of an MR imaging apparatus, an X-ray imaging apparatus, and a CT imaging apparatus.

For example, the medical imaging apparatus is an MR imaging apparatus. Suitable reflexes for MR imaging may include, but not limited to, the pupil reflex, the superficial reflex and the withdrawal reflex. In one example, the pupil reflex may be measured in an MRI system by repeated interleaving of dedicated iris MR imaging with the conventional scan protocol. In another example, superficial reflexes in response to stroking of the skin may be measured. This may involve a dedicated actuator that may be closely integrated with the imaging modality, e.g. an MR receive coil applied to the patient. Alternatively, remote haptic systems may be used. The reflex is then acquired with a suitable diagnostic imaging method. In a further example, the withdrawal reflex in response to pain may be measured. This may involve an actuator that induces sudden stitching pain or very local temperature-induced pain and that is closely integrated with the imaging modality, e.g. a pinching device integrated with a patient support or an MR receive coil applied to the patient. The reflex is then acquired with the MR imaging.

For example, the medical imaging apparatus is an X-ray imaging apparatus or a CT imaging apparatus. Suitable reflexes for X-ray imaging or CT imaging may include, but not limited to, the superficial reflex and the withdrawal reflex, which may be stimulated with similar methods as for MR imaging. The X-ray imaging apparatus or CT imaging apparatus may acquire a series of low-resolution scout images of induced motion of a body part of the patient to detect a response reaction of the superficial reflexes and/or the withdrawal reflexes.

It will be appreciated that the measurement of the resting pupil size (MAX) for pupil reflex does not require any stimulus. However, for other reflexes, such as superficial reflexes and withdrawal reflexes, the method may involve an extra step (not shown) of activating at least one stimulus generator to stimulate a response reaction of these reflexes.

In step 220, a sedation level of the patient is determined based on the detected response reaction. Any appropriate set of image processing methods may be to evaluate the response reaction, e.g., the pupil diameter and/or the induced motion of the stimulated body part, and determine, based on the detected response reaction, a sedation level of the patient.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfil the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A medical imaging system, comprising:
a medical imaging apparatus configured to perform diagnostic imaging of a patient, the medical imaging apparatus comprising a magnetic resonance (MR) imaging apparatus, an X-ray imaging apparatus, or a computed tomography (CT) imaging apparatus; and
a sedation assessment apparatus; wherein the medical imaging apparatus is configured to acquire a sequence of images of a body part of the patient to detect an anatomical motion response reaction of at least one reflex of the patient during the diagnostic imaging carried out by the medical imaging apparatus;
wherein the at least one reflex is selected from reflexes with an anatomical motion response reaction that is in dependence on a sedation depth; and
wherein the sedation assessment apparatus is configured to determine a sedation level of the patient, based on the anatomical motion response reaction detected by the medical imaging apparatus, without use of an additional sensor.

2. The system according to claim 1, wherein the at least one reflex comprises a pupil reflex.

3. The system according to claim 2, wherein the medical imaging apparatus is configured to detect a resting size of an iris of the patient for measuring the pupil reflex.

4. The system according to claim 2, wherein the medical imaging apparatus comprises a magnetic resonance imaging, MRI, apparatus.

5. The system according to claim 4, wherein the MR imaging apparatus is configured to apply a dedicated sequence for performing pupillometry.

6. The system according to claim 5, wherein the dedicated sequence is a T2w-turbo spin echo sequence that uses slice-selective refocusing pulses in a phase encoding direction.

7. The system according to claim 1, wherein the at least one reflex comprises a superficial reflex.

8. The system according to claim 7, further comprising: at least one stimulus generator configured to generate at least one stimulus at an impact region on a patient's skin to stimulate a response reaction of the at least one reflex.

9. The system according to claim 7, wherein the superficial reflex comprises at least one of a normal plantar response and a glabellar reflex.

10. The system according to claim 9, wherein the at least one stimulus generator comprises one or more of the following devices to stimulate the normal plantar response: a stroking device that is attachable to a sole of a foot of the patient; and a remote haptic device configured to induce, from a distance, a haptic sensation at an impact region on a sole of a foot of the patient.

11. The system according to claim 9, wherein the at least one stimulus generator comprises one or more of the following devices to stimulate the glabellar reflex: a device configured to repetitive tap on a forehead of the patient; and a remote haptic device configured to induce, from a distance, a haptic sensation at an impact region on a forehead of the patient.

12. The system according to claim 10, wherein the remote haptic device comprises at least one of the following transmitters: i) a mid-air acoustic transmitter; ii) mid-air ultrasound haptic transmitter; iii) an air nozzle; iv) an electromagnetic wave transmitter; v) an electric transmitter; vi) a magnetic transmitter; or vii) a radio-frequency transmitter.

13. The system according to claim 1, wherein the at least one reflex comprises a withdrawal reflex.

14. The system according to claim 13, further comprising: at least one stimulus generator configured to generate at least one stimulus at an impact region on a patient's skin to stimulate a response reaction of the at least one reflex.

15. The system according to claim 14, wherein the at least one stimulus generator is configured to induce at a patient's skin least one of a sudden stitching pain or a local temperature-induced pain at an impact region on to stimulate the withdrawal reflex.

16. A method for assessing a sedation level, comprising: acquiring, with a medical imaging apparatus comprising a magnetic resonance (MR) imaging apparatus, an X-ray imaging apparatus, or a computed tomography (CT) imaging apparatus, a sequence of images of a body part of a patient to detect an anatomical motion response reaction of at least one reflex of the patient during diagnostic imaging carried out by the medical imaging apparatus; wherein the at least one reflex is selected from reflexes with an anatomical motion response reaction that is in dependence on a sedation depth; and determining a sedation level of the patient based on the anatomical motion response reaction of the at least one reflex detected by the medical imaging apparatus during the diagnostic imaging, without use of an additional sensor.

17. A medical imaging system, comprising:
a medical imaging apparatus configured to perform diagnostic imaging of a subject undergoing a clinical procedure and to acquire a sequence of images of a body part of the subject to detect an anatomical motion response reaction of at least one reflex of the subject during the clinical procedure, wherein the at least one reflex has an anatomical motion response reaction dependent on a sedation depth of the subject, wherein the medical imaging apparatus comprises a magnetic resonance (MR) imaging apparatus, an X-ray imaging apparatus, or a computed tomography (CT) imaging apparatus; and a processor configured to determine a sedation level of the subject based on the anatomical motion response reaction of the at least one reflex detected by the medical imaging apparatus during the diagnostic imaging, without use of an additional sensor.

* * * * *